United States Patent [19]

Bentley

[11] Patent Number: 4,665,257

[45] Date of Patent: May 12, 1987

[54] FACILE, HIGH YIELD SYNTHESIS OF 2,3-DIPHENYL-1,3-BUTADIENE

[75] Inventor: James H. Bentley, Huntsville, Ala.

[73] Assignee: The United States of America as represented by the Secretary of the Army, Washington, D.C.

[21] Appl. No.: 920,650

[22] Filed: Oct. 20, 1986

[51] Int. Cl.$^4$ .............................................. C07C 1/20
[52] U.S. Cl. ...................................... 585/469; 585/25
[58] Field of Search ................................. 585/25, 469

[56] References Cited

U.S. PATENT DOCUMENTS 3,890,278  6/1975  Lehn et al. ........................ 585/428
4,335,055  6/1982  Blaser et al. .

OTHER PUBLICATIONS

Organic Syntheses, vol. 50, p. 62, "2,3-Diphenyl-1,3-Butadiene".
Canadian Journal of Research, vol. 17, Sec. B., pp. 80–82.

Primary Examiner—Curtis R. Davis
Attorney, Agent, or Firm—John C. Garvin, Jr.; Freddie M. Bush

[57] ABSTRACT

A high yield, four step synthesis process is disclosed for producing the monomer, 2,3-diphenyl-1,3-butadiene, wherein in step 1 acetophenone pinacol is produced from the dimerization of acetophenone in 96% yield; in step 2 acetophenone pinacol is reacted with triethoxymethane and benzoic acid to produce 2,3-diphenyl-2-butene in about 88–96% yield. The 2,3-diphenyl-2-butene and N-bromosuccinimide (NBS) are reacted together in step 3 in an ultra violet reactor and in a $CCl_4$ reaction solvent to produce in about 92% yield, the dibromo compound, 1,4-dibromo-2,3-diphenyl-2-butene. In step 4, 1,4-dibromo-2,3-diphenyl-2-butene is converted to the desired monomer in about 86% yield by reacting with NaI under refluxing conditions for about 90 minutes in a hot acetone solution. The monomer 2,3-diphenyl-1,3-butadiene is recovered in hexane, shaken (in the order listed) with water solutions of $NaHSO_3$, $NaHCO_3$, and pure water, dried over $CaCl_2$, and the hexane is spun off. The residue is then recrystallized from hot methyl alcohol by the addition of water. The crystals which are air dried should be refrigerated as soon as possible to prevent spontaneous polymerization.

2 Claims, No Drawings

FACILE, HIGH YIELD SYNTHESIS OF 2,3-DIPHENYL-1,3-BUTADIENE

DEDICATORY CLAUSE

The invention described herein may be manufactured, used, and licensed by or for the Government for governmental purposes without the payment to me of any royalties thereon.

BACKGROUND OF THE INVENTION

The usefulness of a monomer can be projected when the structure's reactive sites suggest an adaptation in certain fields of uses. For example, in the solid propellant field which requires polymers for binders, cross-linking sites are essential for developing propellant integrity and properties. Also, wherever a monomer is used to form structural materials from polymerization, the orientation of the backbone structure and location of unsaturated sites are significant. One such monomer, 2,3-diphenyl-1,3-butadiene, has been projected as an excellent monomer for making head-to-head polystyrene complete with vinyl unsaturation in polymer backbone. Thus, the described structure allows graft additions to be made which results, generally, in a large number of crosslinked polymer types of potential interest as structural materials.

The monomer 2,3-diphenyl-1,3-butadiene, has been synthesized from slow distillation of 2,3-diphenyl-2,3-dihydroxybutane from anhydrous KHSO$_4$ and 2,3-diphenyl-butane-diol as disclosed by Justus Liebig's Annalen der Chemie, Band 570, page 212.

A related process for producing 2,3-diphenyl-1,3-butadiene is disclosed in Organic Syntheses - Vol. 50 by Issei Iwai et al. This disclosure relates to a process wherein the reaction product of anhydrous dimethyl sulfoxide and sodium hydride is reacted with diphenylacetylene in anhydrous dimethyl sulfoxide to produce a low yield (22–25%) of slightly impure 2,3-diphenyl-1,3-butadiene which after recrystallization from methanol gave about 10.7–13.6% of pure 2,3-diphenyl-1,3-butadiene.

The monomer, 2,3-diphenyl-1,3-butadiene, has also been prepared by reaction of 2,3-diphenyl-2,3-dihydroxybutane with acetyl bromide as disclosed by Canadian Journal of Research, Volume 17, Sec. B, page 80.

The first disclosed process has literature reported yields of about 80% of the monomer; however, multiple investigations in carrying out the disclosed process has revealed that great care is required in handling the reaction, and that verification of results reported were not achieved, both in the amount of yield and the monomer produced.

The second disclosed process does not yield a high enough yield of the desired monomer for its commercial acceptance as a starting monomer.

The third disclosed process by the Canadian Journal of Research results in a yield of 20.3%; however, a further improvement in processing to a higher yield of the monomer is desired to render its acceptance as a starting monomer for widespread use.

The monomer, 2,3-diphenyl-1,3-butadiene because of its potential usefulness as a result of the described modifications which can be readily achieved, would have enhanced value as a starting material if it could be made in high yield by a simple process of synthesis.

Therefore, an object of this invention is to provide a facile, high yield synthesis process for producing the monomer, 2,3-diphenyl-1,3-butadiene.

A further object of this invention is to provide a facile, four step process for synthesis of 2,3-diphenyl-1,3-butadiene starting with a compound which can be reacted to produce intermediates for further modification and conversion to the desired monomer.

Still a further object of this invention is to provide a facile, four step process for sythesis of 2,3-diphenyl-1,3-butadiene starting with the dimerization of acetophenone to produce the compound acetophenone pinacol which can be reacted to produce intermediates for further modification and conversion to the desired monomer.

SUMMARY OF THE INVENTION facile, high yield synthesis process of this invention for producing 2,3-diphenyl-1,3-butadiene in four steps starting with the ultra violet driven dimerization of acetophenone to acetophenone pinacol is outlined as follows:

Step 1: Production of 2,3 dihydroxy-2,3-diphenyl butane (Acetophenone Pinacol)

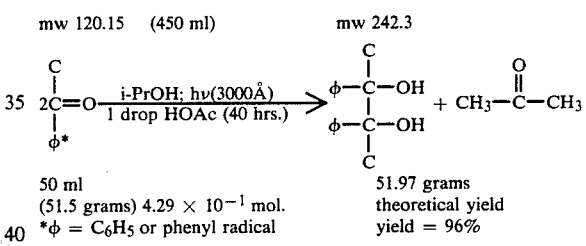

mw 120.15 (450 ml)    mw 242.3

50 ml
(51.5 grams) 4.29 × 10$^{-1}$ mol.
*φ = C$_6$H$_5$ or phenyl radical 51.97 grams
theoretical yield
yield = 96%

Step 2: Production of 2,3-diphenyl-2-butene From Acetophenone Pinacol

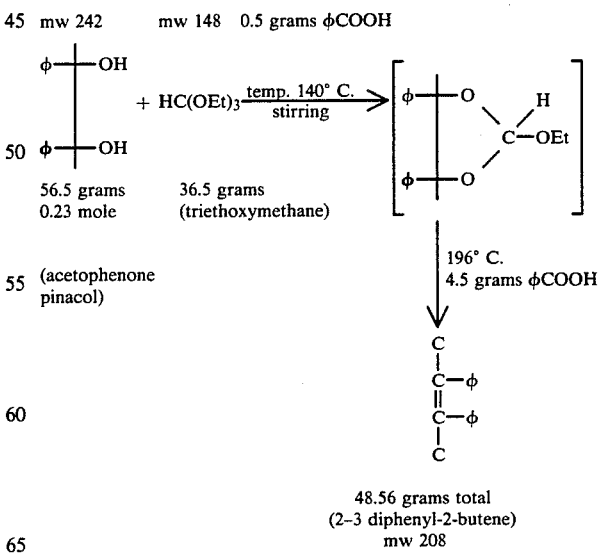

mw 242     mw 148    0.5 grams φCOOH 56.5 grams    36.5 grams
0.23 mole     (triethoxymethane)

(acetophenone pinacol)

196° C.
4.5 grams φCOOH 48.56 grams total
(2–3 diphenyl-2-butene)
mw 208

Step 3: Production of 1,4-dibromo-2,3-diphenyl-2-butene

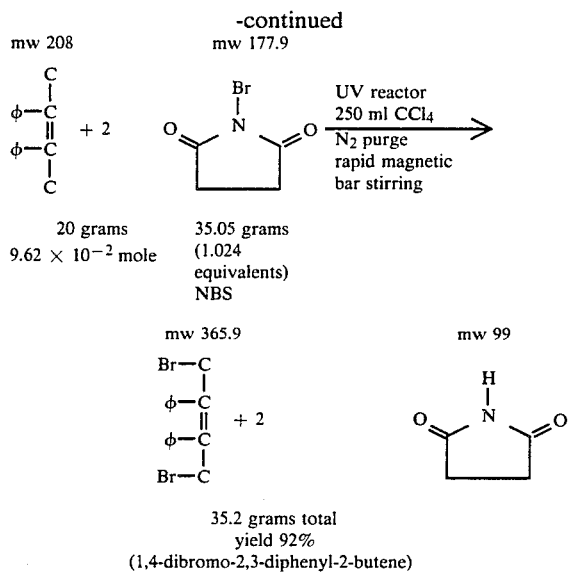

35.2 grams total
yield 92%
(1,4-dibromo-2,3-diphenyl-2-butene)

Step 4: Conversion of 1,4-dibromo-2,3-diphenyl-2-butene to 2,3-diphenyl-1,3-butadiene

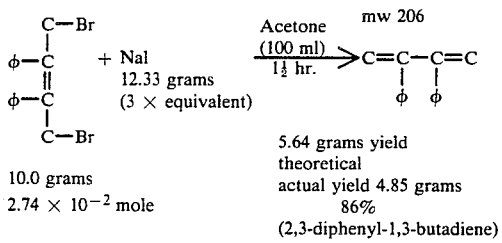

The process outlined above in four steps includes production of intermediates in high yields of 2,3-dihydroxy-2,3-diphenyl butane in step 1; 2,3-diphenyl-2-butene in step 2; and 1,4-dibromo-2,3-diphenyl-2-butene in step 3. Process steps 1 and 3 employ a Rayonet UV reactor with 16 each 3000 Å tubes. Step 3 reaction product, which is a dibromo compound, is subsequently dissolved in hot acetone. A solution of NaI in hot acetone is added, and the dibromo compound is subsequently converted to the desired finished product 2,3-diphenyl-1,3-butadiene. The yields of steps 1, 2, 3, and 4 are about 96%, about 88–96%, about 92%, and about 86% respectively.

DESCRIPTION OF THE PREFERRED EMBODIMENT

The process of this invention for synthesis of 2,3-diphenyl-1,3-butadiene is comprised of a four step procedure wherein the starting compound acetophenone is dimerized under an ultra violet reaction process to yield acetophenone pinacol which is subsequently converted to 2,3-diphenyl-2-butene in the step 2 procedure. The 2,3-diphenyl-2-butene is then reacted with N-bromosuccinimide (NBS) in an ultra violet reactor in a CCl$_4$ reaction solvent to form 1,4-dibromo-2,3-diphenyl-2-butene in the step 3 procedure. The 1,4-dibromo-2,3-diphenyl-2-butene is reacted with NaI in a hot acetone solution to yield 2,3-diphenyl-1,3-butadiene in the step 4 procedure.

Steps 1, 2, 3, and 4 procedures are outlined below, and each reaction equation is followed by a detailed description of the preceding reaction step depicted.

Step 1: Production of 2,3-Dihydroxy-2,3-diphenyl butane (Acetophenone Pinacol)

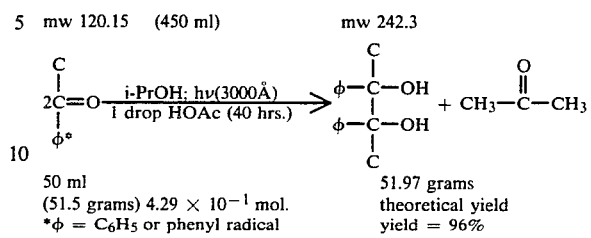

Procedure Step 1

Place acetophenone ($\phi$COCH$_3$), isopropyl alcohol (i-PrOH), and acetic acid (HOAc), into a thoroughly cleaned, free from soap or basic material, quartz reaction flask, along with one magnetic stirring bar. Deaerate liquid and purge ullage with N$_2$. Seal flask and evacuate to $\sim\frac{1}{2}$ atmosphere. Establish stirring and react 40 hrs.

Spin off i-PrOH and acetone (65° C.) and transfer thick liquid to 125 ml Erlenmeyer flask, with the aid of a little i-PrOH (65° C.). Continue to spin off all the volatiles to a final pressure of <1 Torr. Cool flask slightly and add ~30 ml hexanes. Spin at atmospheric pressure to powderize diol (room temp.). Reduce pressure to take off hexanes at room temp. Vacuum dry overnight. The solid may be washed with hexane to eliminate acetophenone odor. The UV reactor is the 16 tube Rayonet type.

Step 2: Production of 2,3-diphenyl-2-butene From Acetophenone Pinacol

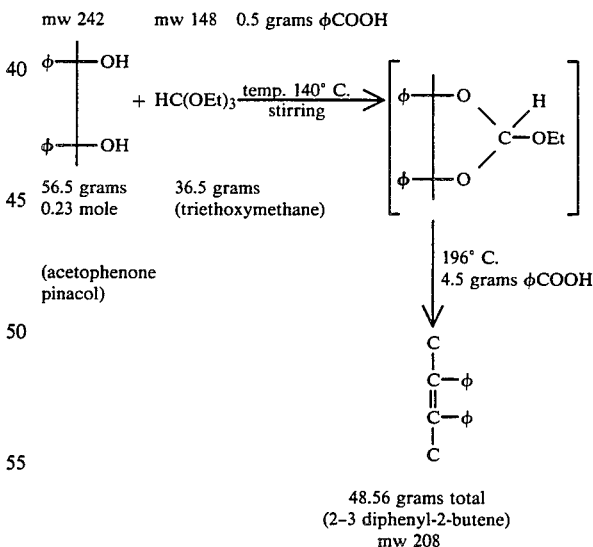

Procedure Step 2

Mix dio, HC(OEt)$_3$, and $\phi$COOH in a 300 ml erlenmeyer flask provided with a magnetic bar stirrer. Place flask with contents in a 140° C. bath and distill out EtOH. As EtOH distillate rate falls to 1 drop every 30 to 45 seconds, remove flask and cool somewhat. Add 4.5 grams of $\phi$COOH and replace flask in bath and elevate temperature to 186° C.–196° C. As temperature passes through ~185° C. decarboxylation begins, accompanied by lots of frothing. After frothing subsides, continue distillation for ~45 minutes. Cool and add 75 ml. CH₂Cl₂; mix well, and separate. Wash twice with H₂O. Dry with CaCl₂, filter, and vacuum dry product, 2,3-diphenyl-2-butene.

Step 3: Production of 1,4-dibromo-2,3-diphenyl-2-butene

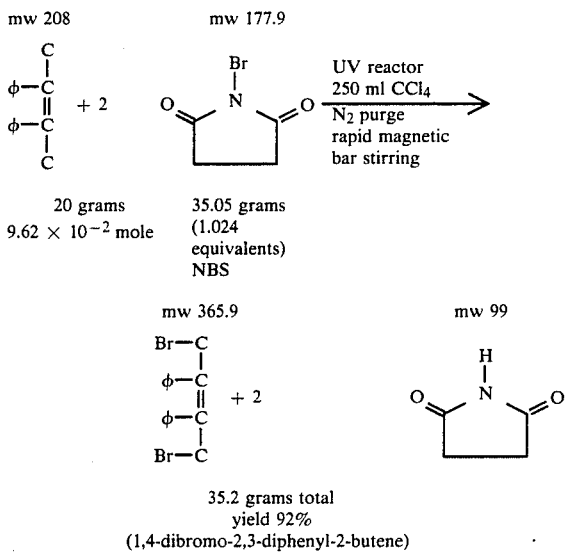

35.2 grams total
yield 92%
(1,4-dibromo-2,3-diphenyl-2-butene)

Procedure Step 3

Place 2,3-dipheyl-2-butene, an egg-shaped magnetic stirring bar, and NBS into a quartz reaction flask. Add CCl₄ and establish stirring. Purge ullage well and seal. Evacuate flask to ~0.5 atmosphere and place into an ultra violet (UV) reactor. Note: The UV reactor is equipped with 3000 Å tubes and is a Rayonet 16 tube device. React until the NBS has all turned to succinimide. This reaction can take from 0.5 to 1.5 hours or possibly longer. The completeness of the reaction is recognized by observing that all the solution's solid material is floating on top of the CCl₄.

Filter reaction mix while hot from reactor and spin off CCl₄ at 65° C.

Recrystallize product from boiling heptane (about 250 ml) twice.

Step 4: Conversion of 1,4-dibromo-2,3-diphenyl-2-butene to 2,3-diphenyl-1,3-butadiene

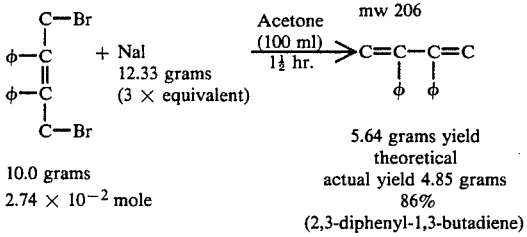

5.64 grams yield theoretical
actual yield 4.85 grams
86%
(2,3-diphenyl-1,3-butadiene)

Procedure Step 4

The clean, recrystallized dibromide is dissolved in hot acetone and a solution of NaI in hot acetone is added. The mix is refluxed for about 90 minutes and the acetone is spun off. The solid is taken up in hexane and any non-soluble materials filtered. The hexane layer is shaken, in order listed, first with a water solutions of NaHSO₃, NaHCO₃, and pure water, and then dried over CaCl₂. The hexane is spun off and the residue is recrystallized from hot methyl alcohol by the addition of water and refrigerated at −15° C. The air dried crystals should be refrigerated as soon as possible to prevent spontaneous polymerization.

I claim:

1. A method for the synthesis of the monomer, 2,3-diphenyl-1,3-butadiene, which comprises completing processes I, II, III, and IV defined hereinbelow, said method beginning with the production of acetophenone pinacol from the dimerization of acetophenone as defined under process I below, followed by the production of 2,3-diphenyl-2-butene from said acetophenone pinacol as defined under process II below, followed by the production of 1,4-dibromo-2,3-diphenyl-2-butene, from said 2,3-diphenyl-2-butene as defined under process III below, and said method being concluded with the conversion of said 1,4-dibromo-2,3-diphenyl-2-butene to said 2,3-diphenyl-1,3-butadiene as defined under process IV below, said method comprising completing steps (i-ix) defined hereinbelow for said process I, completing steps (x-xvii) defined hereinbelow for said process II, completing steps (xviii-xxiv) defined hereinbelow for said process III, and completing steps (xxv-xxxiii) for said process IV as follows:

(i) combining about 51.5 grams of acetophene, 450 milliliters of isopropyl alcohol, and 1 drop of acetic acid to form a reaction mixture in a quartz reactor flask provided with a magnetic stirring bar, said quartz reaction flask being provided with means for operating under vacuum and being transparent to ultra violet light radiation;

(ii) deaerating said reaction mixture and purging ullage with nitrogen gas;

(iii) sealing said reaction flask and evacuating to about one half atmosphere of pressure, placing said evacuated reaction flask in an ultra violet reactor equipped with a plurality of 3000 Å tubes and establishing stirring of said reaction mixture;

(iv) exposing said reaction mixture to the radiation from said plurality of 3000 Å tubes for about 40 hours;

(v) spinning off isopropyl alcohol and acetone reaction product;

(vi) transferring the remaining thick liquid to a reaction flask by aid of a small amount of isopropyl alcohol;

(vii) continuing the spinning off of all volatiles to a final pressure of less than about 1 Torr;

(viii) cooling flask slightly and adding about 30 milliliters of hexane; and, (ix) separating actephenone pinacol after powderizing said acetophenone pinacol following the spinning off of all volatiles at room temperature;

(x) mixing acetophenone pinacol, triethoxymethane, and benzoic acid in a ratio of 56.5 grams: 36.5 grams: 0.5 grams respectively in a reaction vessel provided with a magnetic bar stirrer;

(xi) placing reaction vessel and contents in a 140° C. bath, and completing a reacting and distilling procedure by distilling out ethyl alcohol from reaction vessel until distillate rate falls to 1 drop every 30 to 45 seconds;

(xii) removing said reaction vessel and cooling said reaction vessel and contents somewhat followed by adding and mixing about 4.5 grams of benzoic acid to contents;

(xiii) replacing reaction vessel in a bath and elevating temperature through about 185° C. to about 196° C. to achieve decarboxylation beginning at about 185° C. as evidenced by a high rate of frothing and continuing reaction until frothing subsides;

(xiv) continuing a second distilling procedure for about 45 minutes and followed by cooling;

(xv) adding $Na_2CO_3$ water solution containing about 15 grams $Na_2CO_3$ per 100 milliliters of $H_2O$, boiling for about 1 hour, and cooling;

(xvi) adding about 75 milliliters of $CH_2Cl_2$ followed by mixing well and separating $CH_2Cl_2$ layer;

(xvii) washing $CH_2Cl_2$ layer a plurality of times with $H_2O$ and followed by drying with $CaCl_2$, filtering, and vacuum drying product, 2,3-diphenyl-2-butene;

(xviii) combining and mixing 2,3-diphenyl-2-butene, N-bromosuccinimide, and $CCl_4$ in a ratio of 20.00 grams: 35.05 grams: 250 milliliters to form a reaction mixture respectively in a quartz reaction vessel system provided with a egg shaped magnetic stirring bar;

(xix) Purging ullage well and sealing system prior to pulling vacuum;

(xx) evacuating said quartz reaction vessel system to about 0.5 atmosphere;

(xxi) placing said evacuated quartz reaction vessel system into an ultra violet reactor equipped with a plurality of 3000 Å tubes for reacting from about 0.5 hour to about 1.5 hours or until all the N-bromosuccinimide has changed to succinimide as evidenced by all of solid material floating on top of the $CCl_4$ layer;

(xxii) filtering reaction mixture while hot from said quartz reaction vessel;

(xxiii) spinning off said $CCl_4$ at about 65° C. to separate reaction product;

(xxiv) recrystallizing said reaction product from boiling heptane using about 250 milliliters twice and recovering said reaction product, a recrystallized 1,4-dibromo-2-3-diphenyl-2-butene;

(xxv) dissolving and mixing to form a clear solution of said recrystallized 1,4-dibromo-2-3-diphenyl-2-butene in an amount of about 10.0 grams in about 100 milliliters of hot acetone;

(xxvi) adding a solution of about 12.33 grams of NaI in about 100 milliliters of hot acetone to said 1,4-dibromo-2-3-diphenyl-2-butene in hot acetone solution to form a solution for refluxing;

(xxvii) refluxing said 1,4-dibromo-2-3-diphenyl-2-butene-NaI- hot acetone solution for about 90 minutes;

(xxviii) spinning off acetone from solids;

(xxix) adding hexane to said solids followed by filtering off any non-soluble materials and recovering hexane layer;

(xxx) shaking said hexane layer in order listed, first with water solutions of $NaHSO_3$, $NaHCO_3$ and pure water followed by drying over $CaCl_2$;

(xxxi) spinning off hexane and recrystallizing residue from methyl alcohol by adding $H_2O$ and refrigerating at −15° C. and recovering product, 2,3-diphenyl-1,3-butadiene;

(xxxii) air drying said recovered product, 2,3-diphenyl-1,3-butadiene, and forming crystals; and (xxxiii) refrigerating air dried crystals of said 2,3-diphenyl-1,3-butadiene immediately to prevent spontaneous polymerization.

2. The method of claim 1 wherein said ultra violet reactor of said process I and said process III is each equipped with about 16 tubes.

* * * * *